United States Patent [19]
Knerr et al.

[11] Patent Number: 5,945,129
[45] Date of Patent: Aug. 31, 1999

[54] PROCESS FOR THE PRODUCTION OF AN INFUSION OR DIALYSIS SOLUTION CONTAINING BICARBONATE

[75] Inventors: Thomas Knerr, St. Wendel; Thomas Wild, Eppelborn, both of Germany

[73] Assignee: Fesenius Medical Care Deutschland GmbH, Bad Homburg, Germany

[21] Appl. No.: 08/904,385

[22] Filed: Aug. 1, 1997

[30] Foreign Application Priority Data

Aug. 1, 1996 [DE] Germany ............... 196 31 124

[51] Int. Cl.$^6$ ............... A61K 33/14; A61K 33/10; A61K 33/70; A61K 31/19; A61K 31/70
[52] U.S. Cl. ............... 424/676; 424/686; 514/23; 514/557
[58] Field of Search ............... 424/676, 686; 514/557, 23

[56] References Cited

U.S. PATENT DOCUMENTS 4,489,535  12/1984  Veltman ............... 53/431

FOREIGN PATENT DOCUMENTS

| | | |
|---|---|---|
| 0 339 549 | 2/1989 | European Pat. Off. . |
| 0 399 549 | 11/1990 | European Pat. Off. . |
| 0 437 274 | 7/1991 | European Pat. Off. . |
| 0 490 307 | 6/1992 | European Pat. Off. . |
| 0 564 672 | 6/1996 | European Pat. Off. . |
| 2 467 599 | 4/1981 | France . |
| WO 96/01118 | 1/1996 | WIPO . |

OTHER PUBLICATIONS

Bronswijk et al., "Cytotoxic Effects of Commercial Continuous Ambulatory Peritoneal Dialysis (CAPD) Fluids and of Bacterial Exoproducts on Human Mesothelial Cells In Vitro," Peritoneal Dialysis International, vol. 9, 1989, pp. 197–202.

Witowski et al., "Effect of lactate–buffered peritoneal dialysis fluids on human peritoneal mesothelial cell interleukin–6 and prostaglandin synthesis," Kidney International, vol. 46, 1994, pp. 282–293.

Schambye et al., "The Cytotoxicity of Continuous Ambulatory Peritoneal Dialysis Solutions with Different Bicarbonate/Lactate Ratios," Peritoneal Dialysis International, vol. 13, Supplement 2, 1993, pp. S116–S118.

*Primary Examiner*—Kevin E. Weddington
*Attorney, Agent, or Firm*—Kenyon & Kenyon

[57] ABSTRACT

The invention relates to a process for the production of an infusion or dialysis solution containing bicarbonate and having a physiologically tolerable pH. In order to retain a solution with a stable physiologically tolerable pH even after heat treatment for sterilization, according to the invention, at least 2 mmol/L of at least one carboxylic acid ester is introduced into the solution beforehand. The solution is subjected to heat treatment above 100° C., so that the carboxylic acid ester decomposes almost completely into carboxylic acid and alcohol. The invention further relates to a use of the process according to the invention for the production of a solution for peritoneal dialysis and a medicinal infusion or dialysis solution.

32 Claims, No Drawings

PROCESS FOR THE PRODUCTION OF AN INFUSION OR DIALYSIS SOLUTION CONTAINING BICARBONATE

FIELD OF THE INVENTION

The invention relates to a process for the production of an infusion or dialysis solution containing bicarbonate and having a physiologically tolerable pH, use of this process for the production of a peritoneal dialysis solution and an infusion or dialysis solution, preferably a peritoneal dialysis solution.

BACKGROUND OF INVENTION

In patients with acute or chronic kidney failure, impaired renal function must be compensated by alternative processes. Such alternative processes are hemodialysis and peritoneal dialysis. In continuous ambulatory peritoneal dialysis (CAPD), as it is called, the peritoneal cavity of patients with kidney disease is filled with a fresh peritoneal dialysis solution several times a day. In this type of dialysis, detoxification and dehydration occurs via the peritoneal membrane lining the entire abdominal cavity. In the exchange of substances the peritoneum forms a semipermeable membrane which the dissolved substances pass through by diffusion. Within two to three hours, as a result of diffusion there is a concentration increase, in the freshly filled peritoneal dialysis solution, of the substances usually excreted with the urine.

At the same time, the fluid is removed by ultrafiltration in accordance with the osmotic balance. The peritoneal dialysis solution remains in the abdominal cavity for 4 to 8 hours and is then drained to the outside through a catheter. As a rule, this procedure occurs four times a day, i.e., except for the inflow and outflow times, the peritoneal cavity is constantly filled with solution.

In addition to electrolytes and the osmotically active substance or substances, CAPD solutions contain a buffer substance, which regulates the acid-base metabolism of the patient, and, in particular, is intended to prevent or correct acidosis. Heretofore, sodium lactate has essentially been used to effect buffering. But studies of the biocompatibility of CAPD solutions have shown that solutions containing lactate have a negative effect on the vital function of human cells (cf., e.g., Bronswijk, Verbrugh, Bos, Heezius, Oe, van der Meulen, Verhoef: Cytotoxic effects of commercial continuous ambulatory peritoneal dialysis (CAPD) fluids, *Peritoneal Dialysis International* 9:197-202, 1989; or Witowski, Topley, Jorres: Effect of lactate-buffered peritoneal dialysis fluids on human peritoneal mesothelial cell interleukin-6 and prostaglandin synthesis, *Kidney International* 46:282–293, 1994). Bicarbonate-containing CAPD solutions with a physiological pH have proven to be better tolerated (cf., e.g., Schambye, Pederson, Christensen, Berthelsen, Wang: The cytotoxicity of CAPD solutions with different bicarbonate/lactate ratios, *Peritoneal Dialysis International* 13 (Suppl. 2):116–118, 1993).

From EP 0 339 549, a CAPD solution is known which is produced by mixing two compartments, one of which contains bicarbonate ions. The resulting solution mix has a physiological pH in the 7.2 to 7.4 range and contains 20 to 40 mmol/L bicarbonate ions. Production of the solution containing bicarbonate is difficult because after dissolution of the salt, carbon dioxide always forms in balance according to the following formula:

(1) $2HCO_3^- \leftrightarrows CO_2 + CO_3^{2-} + H_2O$

Carbon dioxide can leave the solution during preparation, stirring, and storage, which leads to an increase in the pH. In order to maintain the pH within the desired pH range, carbon dioxide or some other acid must be regularly added to the solution before filling. In the latter case, however, the bicarbonate content drops, which presents a problem with regard to the declared content and, hence, with regard to the usability of the solution for CAPD.

CAPD solutions are mostly filled into flexible plastic containers which are then subjected to sterilization with superheated steam. Although sheets with a barrier effect against $CO_2$ are available, this process unavoidably results in the loss of $CO_2$ and an increase in the pH. A further difficulty with the CAPD solution is that when the pH is too high, carbonate develops, which forms a relatively insoluble precipitate, for example in the form of a calcium carbonate deposit, with electrolytes present in the solution, especially calcium ions. Adjustment of the pH is therefore of decisive importance for the stability of the solution. Known from EP 564 672 A1 is a peritoneal dialysis solution of physiological composition with regard to the pH, in which the stability of the pH is improved. This peritoneal dialysis solution is obtained directly before use from two single solutions, with the first single solution containing an osmotically active substance and the second single solution containing bicarbonate ions. The first single solution contains anions of mono- and/or dicarboxylic acid and has a pH of 4.5 to 5.8, and the second single solution contains an amino-acid component or a peptide component and has a pH of 7.2 to 10.0. The solution ready for use contains 23 to 26 mmol/L of bicarbonate ions. With this previously known peritoneal dialysis solution it is still necessary to mix together the solution finally used from the separately prepared single solutions and then to use it within a short time.

The considerations referred to above with regard to peritoneal dialysis can generally be carried over to an infusion or dialysis solution containing bicarbonate.

Common to all processes is that, within the context of sterilization with superheated steam or heat sterilization to be undertaken, $CO_2$ escapes and the pH therefore increases.

Object and Summary of the Invention

The object of the invention is, therefore, to develop a process for the production of an infusion or dialysis solution containing bicarbonate and having a physiologically tolerable pH, in which the suitably adjusted pH undergoes as little fluctuation as possible.

Starting from a generic process, the object of the invention is attained by the features of claim 1, according to which, carboxylic acid ester is introduced into the solution beforehand and the solution is subjected to a heat treatment at above 100° C., so that the carboxylic acid ester is almost completely decomposed to carboxylic acid and alcohol.

The carboxylic acid esters introduced are neutral derivatives of carboxylic acids. Water-soluble carboxylic acid esters are hydrolyzed at varying rates depending on the pH of the solution and the temperature, in accordance with the following equation.

(2) carboxylic acid ester + water $\leftrightarrows$ carboxylic acid + alcohol

At increased temperature the hydrolysis takes place rapidly and quantitatively. If the solution is subjected to heat treatment at above 100° C., as occurs in sterilization with superheated steam, one can start with an approximately quantitative hydrolyzation of the carboxylic acid ester.

When hydrolysis of the carboxylic acid ester occurs in the presence of a base, the carboxylic acid obtained according to Equation (2) forms the corresponding salt. If, for example, the base is sodium bicarbonate, the sodium salt of carboxylic acid and carbon dioxide are formed according to Equation (3). With hydrolysis of the ester, the solution is therefore acidified.

(3) carboxylic acid + $NaHCO_3$ ⇌ sodium salt of carboxylic acid + $CO_2$

As a result of the above reaction, the pH of the bicarbonate solution can be reliably adjusted according to the invention.

Advantageous embodiments of the process according to the invention result from the subclaims that follow the main claim.

The invention furthermore relates to the use of the aforementioned process according to the invention for the production of a solution for peritoneal dialysis, in which the solution moreover contains an osmotic agent, for example, glucose, as is known from the related art.

Finally, the invention relates to a medicinal infusion or dialysis solution, preferably a peritoneal dialysis solution, which contains at least a combination of the following components: bicarbonate, preferably sodium bicarbonate, a physiologically tolerable carboxylic acid, and a physiologically tolerable alcohol, resulting in adjustment of the pH in the range from 6.9 to 7.8. Other preferred embodiments of this medicinal infusion or dialysis solution further comprise adding at least 2 mmol/L, preferably 2 to 10 mmol/L, of carboxylic acid ester beforehand. In another preferred embodiment the carboxylic acid ester is ethyl lactate. Preferably, the carboxylic acid derives from the group consisting of acetic acid, propanoic acid, lactic acid, pyruvic acid, 4-hydroxybutyric acid, succinic acid, maleic acid, fumaric acid, malic acid, oxalacetic acid, glutaric acid, 2-oxoglutaric acid, citric acid, isocitric acid and gluconic acid. Preferably, an osmotically active substance, more preferably glucose, is contained in the solution. In another preferred embodiment, the solution is obtained before use by mixing a solution that contains calcium ions with a second solution that contains sodium carbonate. In yet another preferred embodiment, the solution is obtained before use by mixing a solution that contains an osmotically active substance, preferably glucose, with a second solution that contains bicarbonate.

Additional details and advantages of the invention emerge from the following more detailed examples:

In a comparative example, 10 mmol/L ethyl lactate in a solution of 60 mmol/L sodium bicarbonate was examined for 24 hours at room temperature to determine the degree of hydrolysis of the ester according to the following Equation (Equation 4):

(4) ethyl lactate + water ⇌ lactic acid + ethanol

At room temperature, only approximately 6% of the ester was hydrolyzed during 24 hours in this study.

Compared to this, the above-mentioned solution was heated to 121° C. This corresponds to the conditions of superheated steam sterilization. The result is shown in Table 1.

TABLE 1

| Sterilization time | Starting value [ppm] | Ethyl lactate [ppm] | Degree of hydrolysis |
|---|---|---|---|
| 5 min | 1181 | 287 | 76% |
| 10 | 1181 | 107 | 91 |
| 20 | 1181 | 2.7 | 99.8 |
| 30 | 1181 | <1 | >99.9 |

It is clear from Table 1 that after approximately 20 minutes the ester is hydrolyzed close to quantitatively.

In the example cited here, in addition to lactic acid, the corresponding salt of the carboxylic acid, namely sodium lactate, will also form in the presence of sodium bicarbonate. According to Equation 5, we have:

(5) lactic acid + $NaHCO_3$ ⇌ sodium lactate + $CO_2$

Listed in Table 2 are examples of pH values obtained in the bicarbonate solution when various carboxylic acid esters are introduced in various concentrations. These examples are not to be construed as limiting the use of certain carboxylic acid esters or certain concentrations of these esters within the context of the present invention.

As an alternative to carboxylic acid ester, carbonic esters can also be introduced which, upon saponification, can become $H_2CO_3$, or water and carbon dioxide.

(6) carbonic ester + $H_2O$ ⇌ alcohol + carbon dioxide → $H_2O + CO_2$

In the sense of the invention, carbonic ester is to be subsumed under carboxylic acid ester, and, respectively, carbonic acid under carboxylic acids.

The solutions underlying the experimental results reproduced in Table 2 were filled into 1l plastic bags. The filled bags were autoclaved at a temperature of 121° C. After the autoclave temperature was reached, it was maintained for 30 minutes. The pH values found after sterilization are listed in Table 2.

TABLE 2

| Experiment No. | $NaHCO_3$ concentration | Type and concentration of the carboxylic acid ester | pH level after sterilization |
|---|---|---|---|
| 1 | 50 mmol/L | glucono-δ-lactone 5 mmol/L | 7.76 |
| 2 | 50 mmol/L | glucono-δ-lactone 10 mmol/L | 7.23 |
| 3 | 50 mmol/L | diethyl succinate 3 mmol/L | 7.50 |
| 4 | 50 mmol/L | diethyl succinate 5 mmol/L | 7.25 |
| 5 | 55 mmol/L | diethyl tartrate 5 mmol/L | 7.22 |
| 6 | 55 mmol/L | triethyl citrate 3.5 mmol/L | 7.50 |
| 7 | 55 mmol/L | ethyl lactate 10 mmol/L | 7.20 |
| 8 | 55 mmol/L | diethyl carbonate 5 mmol/L | 7.70 |
| 9 | 60 mmol/L | ethyl lactate 10 mmol/L | 7.20 |

We claim:

1. A process for the production of a solution containing bicarbonate ions comprising the steps of combining a carboxylic acid ester with a salt of bicarbonate and heating the solution to a temperature greater than 100° C.

2. The process of claim 1 wherein the carboxylic acid ester is an ester of a carboxylic acid selected from the group consisting of acetic acid, propanoic acid, lactic acid, pyruvic acid, 4-hydroxybutyric acid, succinic acid, maleic acid, fumaric acid, malic acid, oxalacetic acid, glutaric acid, 2-oxoglutaric acid, citric acid, isocitric acid, and gluconic acid.

3. The process of claim 1 wherein the carboxylic acid ester is an ester of a carbonic acid.

4. The process of claim 1 wherein the salt of bicarbonate is sodium bicarbonate.

5. A process for introducing a dialysis solution to a patient in need thereof, comprising providing a solution according to claim 1, and introducing the solution to a patient.

6. A process for introducing a peritoneal dialysis solution to a patient in need thereof, comprising providing a solution according to claim 1, and introducing the solution to a patient.

7. A process for introducing an infusion to a patient in need thereof, comprising providing a solution according to claim 1, and introducing the solution to a patient.

8. A process for introducing a medicinal infusion to a patient in need thereof, comprising providing a solution according to claim 1, and introducing the solution to a patient.

9. The process of claim 1 wherein the solution has a physiologically tolerable pH.

10. The process of claim 1 wherein the carboxylic acid ester is an ester of a monovalent or polyvalent alcohol.

11. The process of claim 1 wherein the carboxylic acid ester is an ester of ethanol, propanol, isopropanol, or glycerol or a cyclic ester (lactone).

12. The process of claim 1 wherein the carboxylic acid ester is selected from the group consisting of glucono-δ-lactone, diethyl succinate, diethyl tartrate, diethyl citrate, ethyl lactate, diethyl carbonate.

13. The process of claim 12 wherein the carboxylic acid ester is present at a concentration of between about 2 to 10 mmol per liter of solution.

14. The process of claim 13 wherein the pH of the final solution is about 6.9 to 7.8.

15. The process of claim 14 further comprising adding an osmotic agent to the solution.

16. A process for the production of a peritoneal dialysis solution having a pH from about 6.9 to 7.8 containing bicarbonate, a physiologically tolerable carboxylic acid and a physiologically tolerable alcohol comprising the steps of combining a solution containing about 2 to 10 mmol/L of a carboxylic acid ester with a solution containing about 50 to 60 mmol/L of a salt of bicarbonate and heating the solution to greater than 100° C.

17. The process of claim 16 wherein the carboxylic acid ester is a carbonic ester.

18. The process of claim 16 wherein the salt of bicarbonate is sodium bicarbonate.

19. The process of claim 16 wherein the carboxylic acid ester is an ester of a monovalent or polyvalent alcohol.

20. The process of claim 16 wherein the carboxylic acid ester is an ester of ethanol, propanol, isopropanol, or glycerol or a cyclic ester (lactone).

21. The process of claim 16 wherein the carboxylic acid is selected from the group consisting of acetic acid, propanoic acid, lactic acid, pyruvic acid, 4-hydroxybutyric acid, succinic acid, maleic acid, fumaric acid, malic acid, oxalacetic acid, glutaric acid, 2-oxoglutaric acid, citric acid, isocitric acid, and gluconic acid.

22. The process of claim 16 wherein the carboxylic acid ester is selected from the group consisting of glucono-δ-lactone, diethyl succinate, diethyl tartrate, diethyl citrate, ethyl lactate, or diethyl carbonate.

23. The process of claim 16 further comprising adding an osmotic agent to the final solution.

24. The process of claim 16 wherein the osmotic agent is glucose.

25. A medicinal infusion or dialysis solution, preferably a peritoneal dialysis solution with a pH in the range of 6.9 to 7.8 comprising at least: bicarbonate, preferably sodium bicarbonate, a physiologically tolerable carboxylic acid and a physiologically tolerable alcohol.

26. The solution according to claim 25 wherein at least 2 mmol/L, preferably 2 to 10 mmol/L, of a carboxylic acid ester is introduced beforehand.

27. The solution according to claim 25 wherein the carboxylic acid derives from the group of acetic acid, propanoic acid, lactic acid, pyruvic acid, 4-hydroxybutyric acid, succinic acid, maleic acid, fumaric acid, malic acid, oxalacetic acid, glutaric acid, 2-oxoglutaric acid, citric acid, isocitric acid, and gluconic acid.

28. The solution according to claim 26 wherein the carboxylic acid ester is ethyl lactate.

29. The solution according to claim 25 further comprising adding an osmotically active substance.

30. The solution according to claim 25 further comprising adding glucose.

31. The solution according to claim 25 further comprising obtaining the solution immediately before use by mixing a solution containing calcium ions with a solution containing sodium carbonate.

32. The solution according to claim 29 further comprising obtaining the solution before use by mixing a solution containing an osmotically active substance with a second solution containing bicarbonate.

* * * * *

UNITED STATES PATENT AND TRADEMARK OFFICE
CERTIFICATE OF CORRECTION

PATENT NO. : 5,945,129
DATED : August 31, 1999
INVENTOR(S) : Thomas Knerr and Thomas Wild It is certified that error appears in the above-identified patent and that said Letters Patent is hereby corrected as shown below:

Column 1, line 67, "2HCO$_3$-" should be changed to -- 2HCO$_3^-$ --.

Signed and Sealed this

Eighteenth Day of July, 2000

Attest:

Q. TODD DICKINSON

*Attesting Officer*        *Director of Patents and Trademarks*